United States Patent
Mousa et al.

(10) Patent No.: US 10,581,099 B2
(45) Date of Patent: Mar. 3, 2020

(54) USE OF NEURAL NETWORK AND EIS SIGNAL ANALYSIS TO QUANTIFY H2 CROSSOVER IN-SITU IN OPERATING PEM CELLS

(71) Applicants: BALLARD POWER SYSTEMS INC., Burnaby (CA); SIMON FRASER UNIVERSITY, Burnaby (CA)

(72) Inventors: Ghassan Hassan Mousa, Jeddah (SA); Jacob William De Vaal, Coquitlam (CA); Farid Golnaraghi, West Vancouver (CA)

(73) Assignees: BALLARD POWER SYSTEMS INC., Burnaby (CA); SIMON FRASER UNIVERSITY, Burnaby (CA)

( * ) Notice: Subject to any disclaimer, the term of this patent is extended or adjusted under 35 U.S.C. 154(b) by 227 days.

(21) Appl. No.: 15/240,944

(22) Filed: Aug. 18, 2016

(65) Prior Publication Data

US 2017/0040626 A1 Feb. 9, 2017

Related U.S. Application Data

(63) Continuation of application No. PCT/US2015/016698, filed on Feb. 19, 2015.
(Continued)

(51) Int. Cl.
*H01M 8/04664* (2016.01)
*H01M 8/0438* (2016.01)
(Continued)

(52) U.S. Cl.
CPC ......... *H01M 8/04679* (2013.01); *G01M 3/40* (2013.01); *H01M 8/04432* (2013.01);
(Continued)

(58) Field of Classification Search
CPC ..... H01M 2008/1095; H01M 8/04432; H01M 8/04455; H01M 8/04649; H01M 8/04679; H01M 8/1018
See application file for complete search history.

(56) References Cited

U.S. PATENT DOCUMENTS

| | | | | |
|---|---|---|---|---|
| 5,397,656 A | * | 3/1995 | Morimoto | .......... H01M 8/0612 429/415 |
| 7,718,286 B2 | | 5/2010 | Fujita | |

(Continued)

FOREIGN PATENT DOCUMENTS

| | | |
|---|---|---|
| CA | 2488564 A1 | 5/2006 |
| CN | 1871733 A | 11/2006 |

(Continued)

OTHER PUBLICATIONS

Andreasen et al., "Characterisation and Modelling of a High Temperature PEM Fuel Cell Stack using Electrochemical Impedance Spectroscopy," *Fuel Cells* 9(4):463-473, 2009.
(Continued)

*Primary Examiner* — Manuel A Rivera Vargas
*Assistant Examiner* — Yaritza H Perez Bermudez
(74) *Attorney, Agent, or Firm* — Seed Intellectual Property Law Group LLP

(57) ABSTRACT

Methods for detecting a hydrogen leak and quantifying a rate of the same in a polymer electrolyte membrane fuel cell stack are provided, as well as a fuel cell diagnostic apparatus that diagnoses a hydrogen leak in a fuel cell stack.

12 Claims, 14 Drawing Sheets

Related U.S. Application Data

(60) Provisional application No. 61/941,927, filed on Feb. 19, 2014.

(51) Int. Cl.

| | |
|---|---|
| *H01M 8/0444* | (2016.01) |
| *H01M 8/04537* | (2016.01) |
| *G01M 3/40* | (2006.01) |
| *H01M 8/1018* | (2016.01) |
| *G01N 27/02* | (2006.01) |
| *G06N 3/08* | (2006.01) |

(52) U.S. Cl.
CPC ... *H01M 8/04455* (2013.01); *H01M 8/04649* (2013.01); *H01M 8/1018* (2013.01); *G01N 27/026* (2013.01); *G06N 3/08* (2013.01); *H01M 2008/1095* (2013.01)

(56) References Cited

U.S. PATENT DOCUMENTS

| | | | |
|---|---|---|---|
| 2006/0074574 A1 | 4/2006 | Gasda et al. | |
| 2007/0166598 A1* | 7/2007 | Joos | H01M 8/04089 429/429 |
| 2009/0035612 A1* | 2/2009 | Suematsu | H01M 8/04089 429/432 |
| 2012/0015268 A1* | 1/2012 | Yoshida | H01M 8/04223 429/429 |
| 2015/0064509 A1* | 3/2015 | Joos | H01M 8/04089 429/9 |

FOREIGN PATENT DOCUMENTS

| | | |
|---|---|---|
| CN | 101107538 A | 1/2008 |
| CN | 103231662 A | 8/2013 |
| EP | 1555708 A2 | 7/2005 |
| JP | 2007-48542 A | 2/2007 |
| TW | I395965 B1 | 5/2013 |
| WO | 2013/083872 A1 | 6/2013 |

OTHER PUBLICATIONS

Brunetto et al., "PEM fuel cell testing by electrochemical impedance spectroscopy," *Electric Power Systems Research* 79:17-26, 2009.

Cano-Castillo et al., "Parameter Changes During Gradual Flooding of a PEM Fuel Cell Through EIS Studies," *ECS Transactions* 3(1):931-939, 2006.

Chen et al., "A method for intelligent fault diagnosis of rotating machinery," *Digital Signal Processing* 14:203-217, 2004.

Ciureanu et al., "Electrochemical Impedance Study of PEM Fuel Cells. Experimental Diagnostics and Modeling of Air Cathodes," *J. Phys. Chem. B* 105:3531-3539, 2001.

Dhirde et al., "Equivalent Electric Circuit Modeling and Performance Analysis of a PEM Fuel Cell Stack Using Impedance Spectroscopy," *IEEE Transactions on Energy Conversion* 25(3):778-786, 2010.

Hsueh, "A Study of Artificial Neural Networks for Electrochemical Data Analysis," *ECS Transactions* 25(28):47-58, 2010.

Huang et al., "Experimental investigation of pinhole effect on MEA/cell aging in PEMFC," *International Journal of Hydrogen Energy* 38:543-550, 2013.

Jardine et al., "A review on machinery diagnostics and prognostics implementing condition-based maintenance," *Mechanical Systems and Signal Processing* 20:1483-1510, 2006.

Jespersen et al., "Electrochemical characterization of a polybenzimidazole-based high temperature proton exchange membrane unit cell," *Journal of Power Sources* 191:289-296, 2009.

Kang et al., "Accelerated test analysis of reversal potential caused by fuel starvation during PEMFCs operation," *International Journal of Hydrogen Energy* 35:3727-3735, 2010.

Kawaji et al., "Microstructure of Platinum-Carbon Agglomerates with Hydrocarbon-Based Binder and Its Effect on the Cathode Performance of PEFC," *Journal of the Electrochemical Society* 158(8):B1042-B1049, 2011.

Kreitmeier et al., "Factors determining the gas crossover through pinholes in polymer electrolyte fuel cell membranes," *Electrochimica Acta* 80:240-247, 2012.

Lin et al., "Investigation of Membrane Pinhole Effects in Polymer Electrolyte Fuel Cells by Locally Resolved Current Density," *Journal of the Electrochemical Society* 158(1)B11-B17, 2011.

Lobato et al., "The neural networks based modeling of a polybenzimidazole-based polymer electrolyte membrane fuel cell: Effect of temperature," *Journal of Power Sources* 192:190-194, 2009.

Makharia et al., "Measurement of Catalyst Layer Electrolyte Resistance in PEFCs Using Electrochemical Impedance Spectroscopy," *Journal of the Electrochemical Society* 152(5):A970-A977, 2005.

Mérida, et al., "Characterisation of proton exchange membrane fuel cell (PEMFC) failures via electrochemical impedance spectroscopy," *Journal of Power Sources* 161:264-274, 2006.

Nakamura et al., "Measurement of Leak Current Generation Distribution in PEFC and Its Application to Load Fluctuation Testing Under Low Humidification," *Electrical Engineering in Japan* 174(1):2011, 9 pages, (translated from *Denki Gakki Ronbunshi* 128-B(11):1371-1378, 2008).

Ou et al., "A hybrid neural network model for PEM fuel cells," *Journal of Power Sources* 140:319-330, 2005.

Rodat et al., "EIS measurements in the diagnosis of the environment within a PEMFC stack," *J Appl Electrochem* 40:911-920, 2010.

Weber, "Gas-crossover and Membrane-pinhole Effects in Polymer-electrolyte Fuel Cells," *Journal of Electrocemical Society* 155(6):B521-B531, 2008, 46 pages.

Wu et al., "An expert system for fault diagnosis in internal combustion engines using wavelet packet transform and neural network," *Expert Systems with Applications* 36:4278-4286, 2009.

Yousfi Steiner et al., "Diagnosis of polymer electrolyte fuel cells failure modes (flooding & drying out) by neural networks modeling," *International Journal of Hydrogen Energy* 36:3067-3075, 2011.

Yousfi Steiner et al., "Model-based diagnosis for proton exchange membrane fuel cells," *Mathematics and Computers in Simulation* 81:158-170, 2010.

Yousfi-Steiner et al., "A review on PEM voltage degradation associated with water management: Impacts, influent factors and characterization," *Journal of Power Sources* 183:260-274, 2008.

Yuan et al., "AC impedance diagnosis of a 500W PEM fuel cell stack Part I: Stack impedance," *Journal of Power Sources* 161:920-928, 2006.

Yuan et al., *Electrochemical Impedance Spectroscopy in PEM Fuel Cells*, Springer-Verlag, London, United Kingdom, 2010, 428 pages.

\* cited by examiner

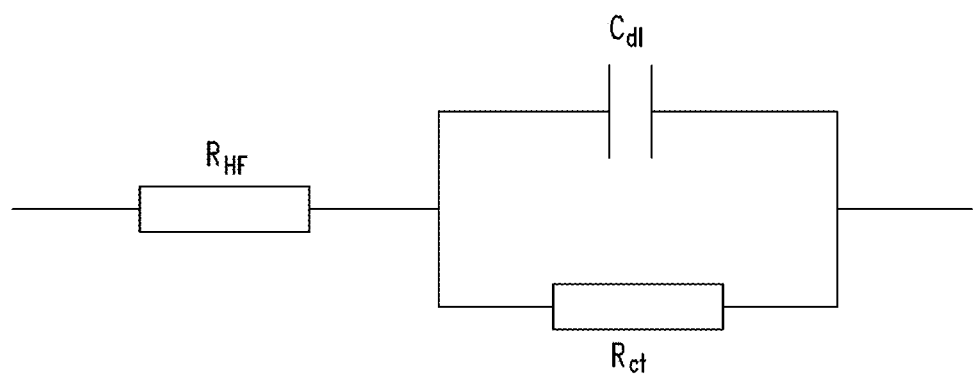
*FIG. 1*   Randles model
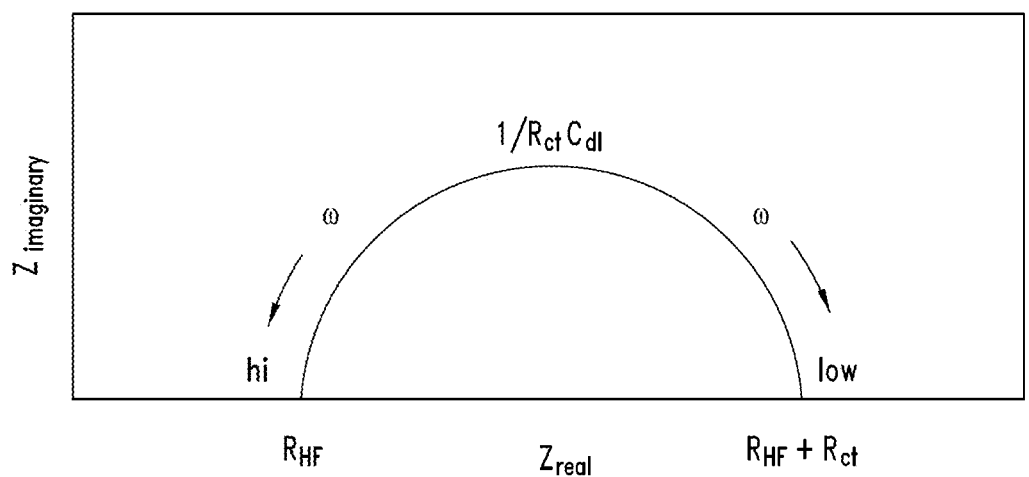
*FIG. 2*   Nyquist plot of a fuel cell

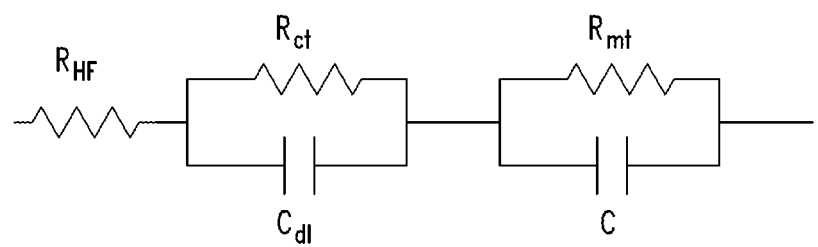
*FIG. 3*  Equivalent FC circuit for expermental fitting

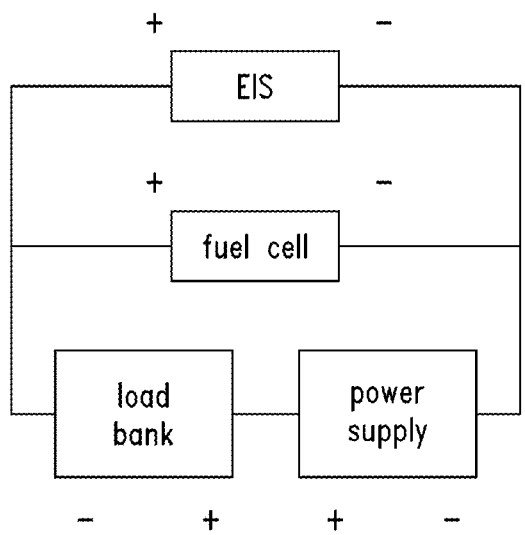
FIG. 5  Schematic view of the test bed
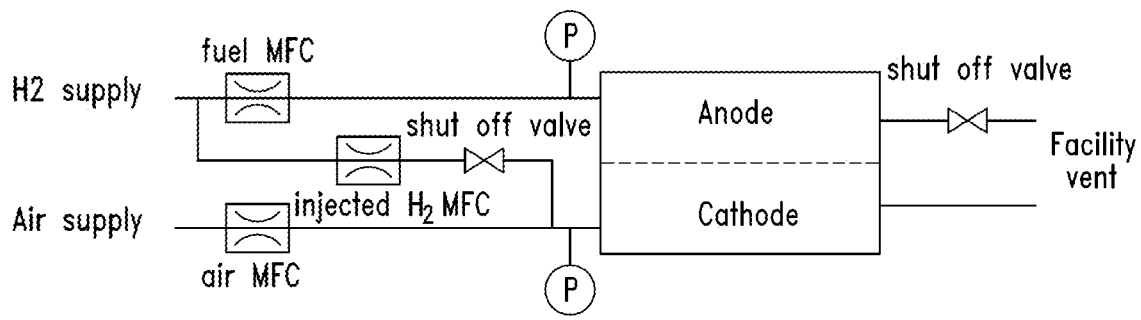
FIG. 6  A schematic diagram of experimental setup
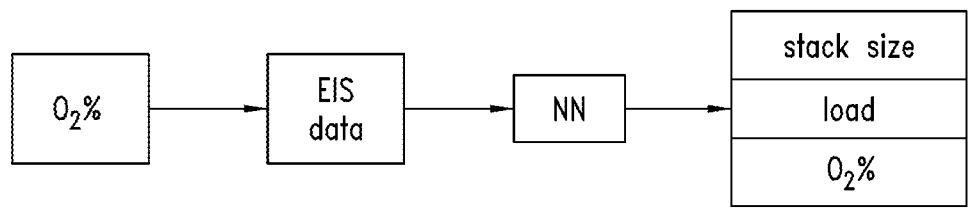
FIG. 7  A schematic diagram of neural network training

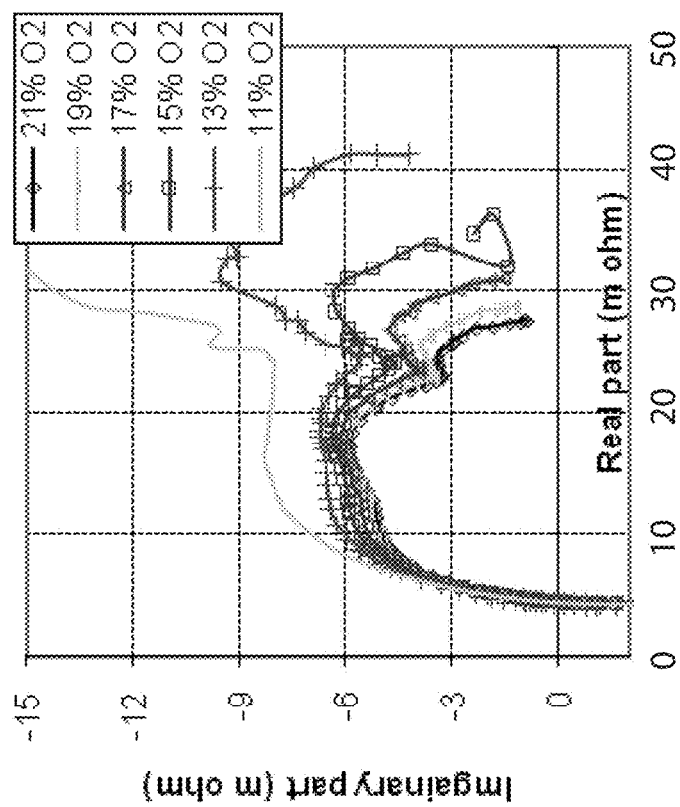
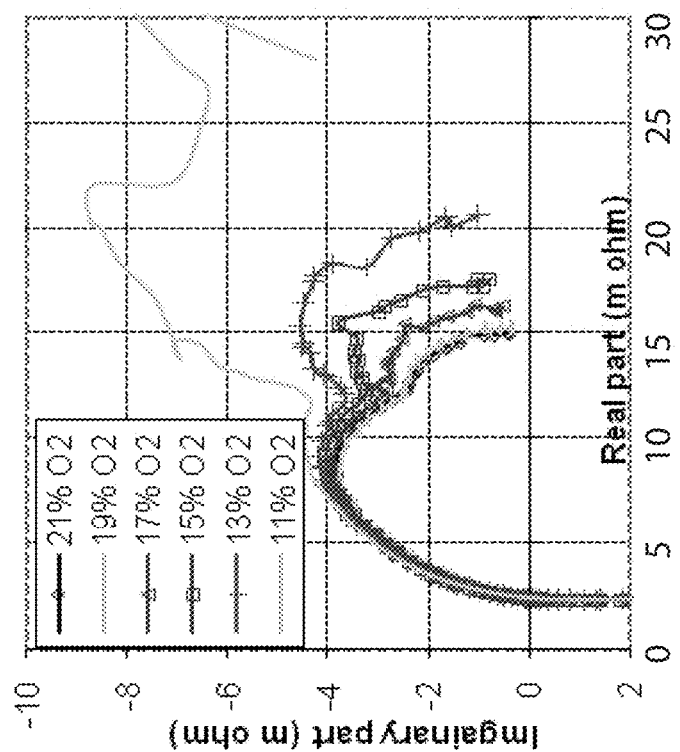
Fig. 8b
Fig. 8a
Oxygen concentration impedance signatures at 20A load of a 5-cells (a) and 9-cells (b) stack

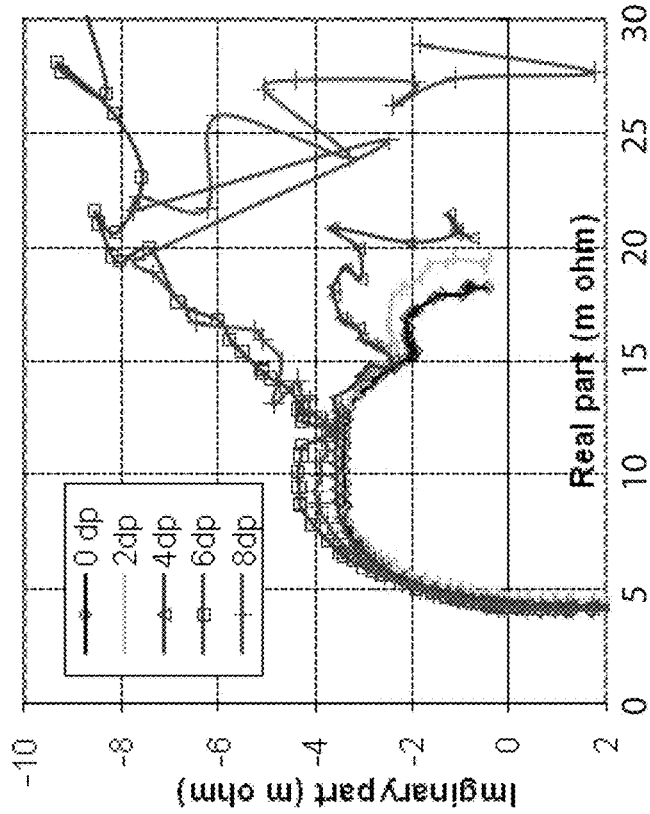
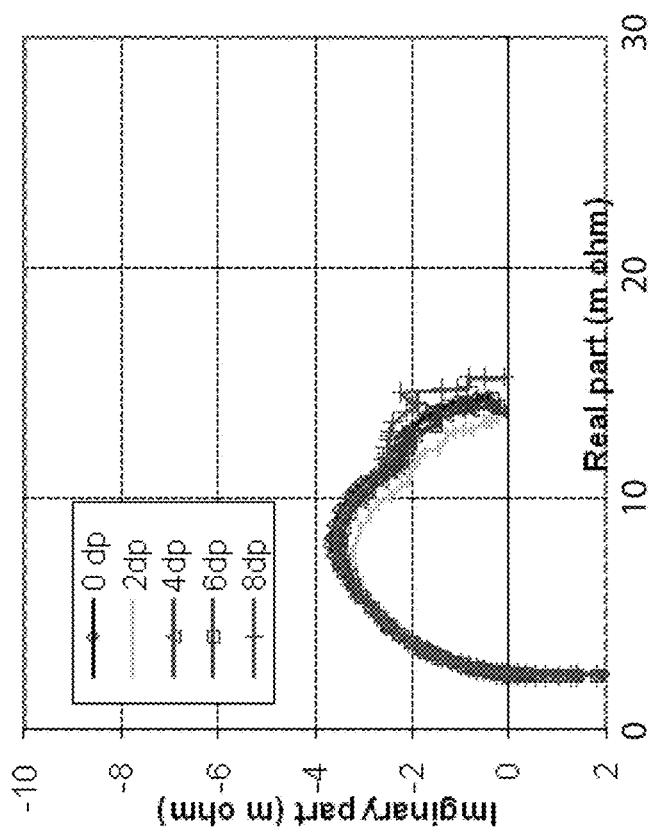
Fig. 9b
Fig. 9a
dP Impedance of a 5-cells stack at 20A load with medium leaky cell (a) and large leaky cell (b)

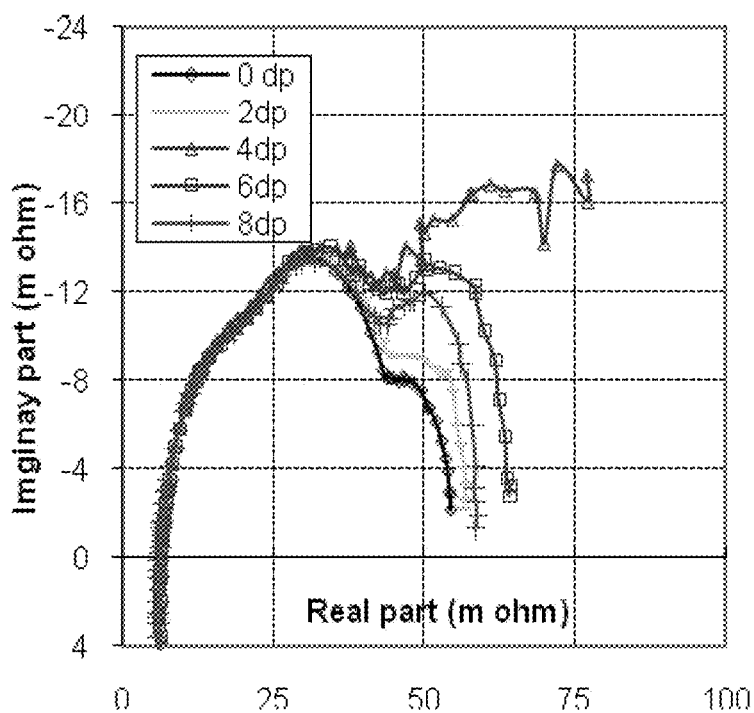
FIG. 10
dP Impedance of a 19-cells stack at 20A load with large leaky cell
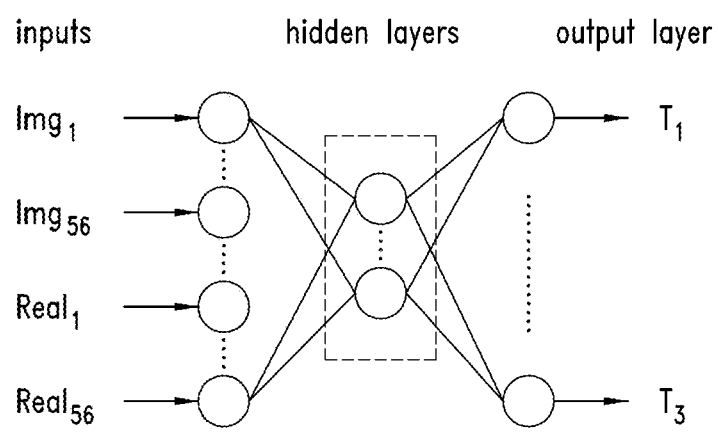
FIG. 11 Neural network topography 62:20:3

Oxygen concentration (left) and hydrogen leak rate (right) of a small leaky cell in n-cells stack Oxygen concentration (left) and hydrogen leak rate (right) of a medium leaky cell in n-cells stack Oxygen concentration (left) and hydrogen leak rate (right) of a large leaky cell in n-cells stack dP Impedance of a single cell and injected hydrogen at 20A load dP Impedance of a single cell and injected hydrogen at 50A load dP versus hydrogen leak rate of a medium leaky cell during off-line dP versus time (left) and hydrogen flow versus time (right)

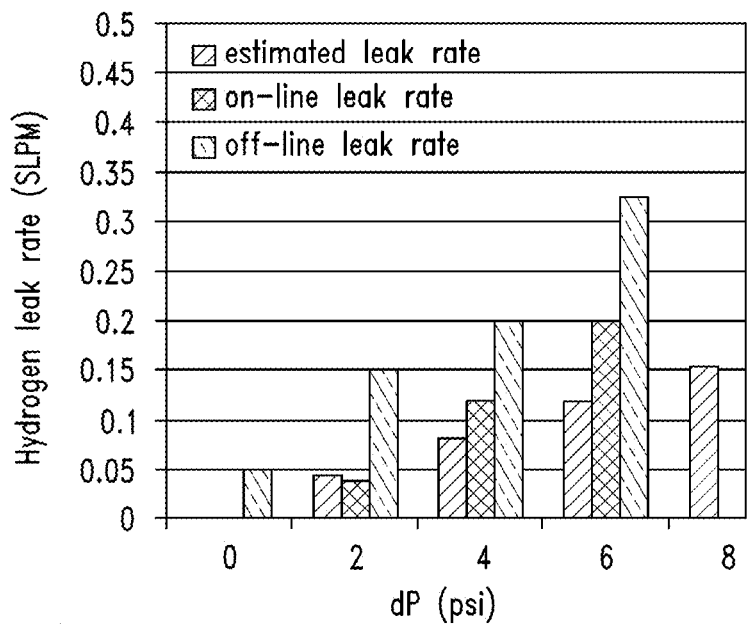
FIG. 19 Measured and estimated leak rates
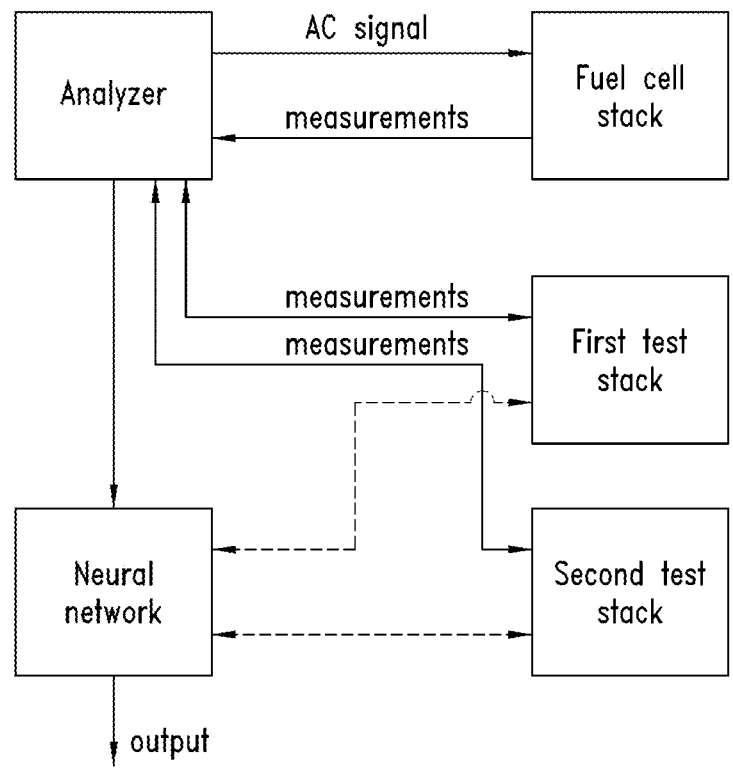
FIG. 20

USE OF NEURAL NETWORK AND EIS SIGNAL ANALYSIS TO QUANTIFY H2 CROSSOVER IN-SITU IN OPERATING PEM CELLS

BACKGROUND

Proton exchange membrane (PEM) fuel cells are one of the most important types of fuel cells due to their ability to work at low temperature, and their low weight and volume. This has made PEM fuel cells a competitive alternative power source in stationary and automotive applications. However, the extensive use of PEM fuel cell depends on its reliability and cost efficiency. Over the years, the fuel cell industry has developed more durable membrane electrode assembly (MEA) to avoid failures and extend the operating lifetime, but PEM fuel cells remain vulnerable to hydrogen leaks which can lead to performance degradation and potential safety issues. While the onset of membrane degradation can be delayed, the initiation of MEA pinholes is inevitable with existing technology measures.

Due to the existence of pinholes in the MEA, hydrogen may leak through the MEA from the anode to the cathode. At sufficient rates of hydrogen cross-over leak, the fuel cell performance drops due to the direct recombination with reactant oxygen on the cathode side. This recombination affects the available amount of oxygen used for the electrochemical reaction. In severe cases, the fuel cell might suffer fuel and/or air starvation. Direct recombination of fuel with oxygen results in the formation of water on the cathode side, leading to air starvation of the affected cell because of the consumption of oxygen and/or water accumulation in the cathode.

Prior work dealing with MEA pinholes is limited. Weber (Adam Z. Weber, "Gas-Crossover and Membrane-Pinhole Effects in Polymer-Electrolyte Fuel Cells", Journal of Electrochemical Society, 155 (6) B521-B531, 2008) developed a mathematical model to simulate the effect of pinholes in a PEM fuel cell. He showed the performance drop in terms of cell voltage and current density. The drop in current density was also considered by Lin et al. (R. Lin, E. Gülzow, M. Schulze and K. A. Friedrich, "Investigation of Membrane Pinhole Effects in Polymer Electrolyte Fuel Cells by Locally Resolved Current Density", Journal of The Electrochemical Society, 158 (1) B11-B17, 2011). Hydrogen leak can also be detected by the increase of leak current and drop in voltage (Soshin Nakamura, Eiichi Kashiwa, Hidetoshi Sasou, Suguru Hariyama, Tsutomu Aoki, Yasuji Ogami and Hisao Nishikawa, "Measurement of Leak Current Generation Distribution in PEFC and Its Application to Load Fluctuation Testing Under Low Humidification", Electrical Engineering in Japan, Vol. 174, No. 1, 2011; B. T. Huang, Y. Chatillon, C. Bonnet, F. Lapicque, S. Leclerc, M. Hinaje, S. Rael, "Experimental investigation of pinhole effect on MEA/cell aging in PEMFC", International journal of hydrogen energy 38: 543-550, 2013). However, detecting small hydrogen leaks by measuring the cell voltage is not feasible, where the degraded voltage is very minimal with the gradual increasing of leak rates.

These studies have also only dealt with a single small-sized MEA. In actual industrial applications, however, larger stacks containing multiple unit cells in series are used to provide large amounts of power; that is, on the order of tens of kilowatts. Because of the large size and a lack of appropriate models, a stack of this size requires a diagnostic tool that is able to detect hydrogen leak in operation and quantify its rate effectively. Knowing the amount of hydrogen leak during fuel cell operation may facilitate the establishment of mitigation criteria to reduce its effect on stack performance.

SUMMARY

One embodiment of the present disclosure is directed to a method that includes determining a hydrogen leak rate in a polymer electrolyte membrane fuel cell stack, the determining including generating a first set of data points for impedance signatures of oxygen concentrations in a first fuel cell test stack, the first fuel cell test stack having no internally leaky cells and generating a second set of data points for impedance signatures of differential pressures of hydrogen and oxygen in a second fuel cell test stack, the second fuel cell test stack having at least one internally leaky cell. The method includes mapping the impedance signatures of the oxygen concentrations from the first set of data points to the impedance signatures of the differential pressures of hydrogen and oxygen from the second set of data points. The method also includes passing an AC signal through the fuel cell stack, detecting impedance signatures from the AC signal in the fuel cell stack, identifying an oxygen concentration of the fuel cell stack by matching the impedance signature from the AC signal with the impedance signature of the oxygen concentration in the first fuel cell test stack, and calculating the hydrogen leak rate of the fuel cell stack by matching the oxygen concentration of the fuel cell stack with the corresponding mapped impedance signature of the differential pressure of the second fuel cell test stack.

The fuel cell stack has specific dimensions. The first fuel cell test stack has substantially similar dimensions to the dimensions of the fuel cell stack and the second fuel cell test stack has substantially similar dimensions to the dimensions of the fuel cell stack. The method also includes quantifying a rate of the hydrogen leak using a neural network.

Another embodiment of the present disclosure, which may be combined with the embodiment described above, includes a method that includes detecting a hydrogen leak in a polymer electrolyte membrane fuel cell stack and quantifying a rate of the hydrogen leak. The quantifying including providing to a neural network a first set of data points that represent impedance signature values based on oxygen concentrations in a first fuel cell test stack, the first test stack having low leakage and providing a second set of data points that represent impedance signature values based on differential pressures of hydrogen and oxygen in a second fuel cell test stack, the second test stack having a higher leakage than the first fuel cell test stack. The quantifying includes generating a map by matching differential pressures from the second fuel cell test stack to oxygen concentrations from the first fuel cell test stack by matching the impedance signature values from the first fuel cell test stack with impedance signature values from the second fuel cell test stack and calculating the hydrogen leak rate of the fuel cell stack by identifying a differential pressure, the identifying of the differential pressure including: detecting an impedance value in the fuel cell stack based on an oxygen concentration; and using the map to identify the differential pressure using the impedance value of the oxygen concentration in the fuel cell stack.

The method also includes passing an AC signal through the fuel cell stack, detecting the impedance value, the impedance value being generated by the AC signal in the fuel cell stack, transmitting the impedance value to the neural network, and identifying the oxygen concentration and differential pressure corresponding to the impedance value using the map of the neural network.

The fuel cell stack has a plurality of plates, each plate having a rectangular shape. The first test stack has a plurality of plates, each plate having the rectangular shape of the plates of the fuel cell stack. The second test stack has a plurality of plates, each plate having the rectangular shape of the plates of the fuel cell stack.

The disclosure also includes a fuel cell diagnostic apparatus that diagnoses a hydrogen leak in a fuel cell stack, the hydrogen leak having a rate, the apparatus including a frequency response analyzer configured to apply an AC signal to the fuel cell stack and configured to measure an output impedance signature, a first fuel cell test stack having impedance signature values associated with oxygen concentrations, a second fuel cell test stack having impedance signature values associated with differential pressures of hydrogen and oxygen, and a neural network configured to receive the impedance signature values from the first fuel cell stack and the impedance signature values from the second fuel cell stack, the neural network configured to map the impedance signature values from the first fuel cell stack and the impedance signature values from the second fuel cell stack to each other, the neural network configured to identify an oxygen concentration from the map based on the output impedance signature from the fuel cell stack and configured to output a differential pressure based on the oxygen concentration, and the neural network configured to calculate the rate of the hydrogen leak from the oxygen concentration and the differential pressure from the map.

This disclosure describes identifying hydrogen leaks in an operational fuel cells and estimating leak rates by (1) mapping the impedance signatures for a set of detected oxygen concentrations in a test stack to impedance signatures for a set of detected differential pressures of hydrogen and oxygen in an internally leaky test stack, (2) detecting an impedance signature for an AC signal passed through the operational fuel cell and identifying the oxygen concentration corresponding to that detected impedance signature, and (3) calculating a hydrogen leak rate of the operational fuel cell from the identified oxygen concentration based on the AC signal.

BRIEF DESCRIPTION OF THE SEVERAL VIEWS OF THE DRAWINGS

The foregoing and other features and advantages of the present disclosure will be more readily appreciated as the same become better understood from the following detailed description when taken in conjunction with the accompanying drawings.

FIG. 1 is a schematic view of a Randles circuit representing operation of a fuel cell;

FIG. 2 is a Nyquist plot of resistance versus reactance of a fuel cell;

FIG. 3 is a schematic view of a modified Randles circuit of FIG. 1;

FIG. 5 schematic diagram of a test arrangement;

FIG. 6 is a schematic diagram of a fuel cell in a testing arrangement as described herein;

FIG. 7 is a schematic diagram of training a neural network;

FIGS. 8a and 8b are graphs of is oxygen concentration impedance signatures with different numbers of fuel cells;

FIGS. 9a and 9b are graphs of impedance of a fuel cell stack with different leakages;

FIG. 10 is a graph of differential pressure impedance of a 19-cell stack with a large leaky cell;

FIG. 11 is a diagram of neural network topography;

FIG. 19 is a graph of measured and estimated hydrogen leak rates;

FIG. 20 is a schematic diagram of a fuel cell diagnostic apparatus;

FIG. 21 is a table showing a test plan for testing normal and leaky cells with different oxygen concentrations;

FIG. 22 is a table showing fuel cell operating conditions for the testing of various oxygen and hydrogen concentrations while maintaining constant flow rates; and FIG. 23 is a table showing target vectors of an n-cells stack network.

DESCRIPTION

Figure 4:
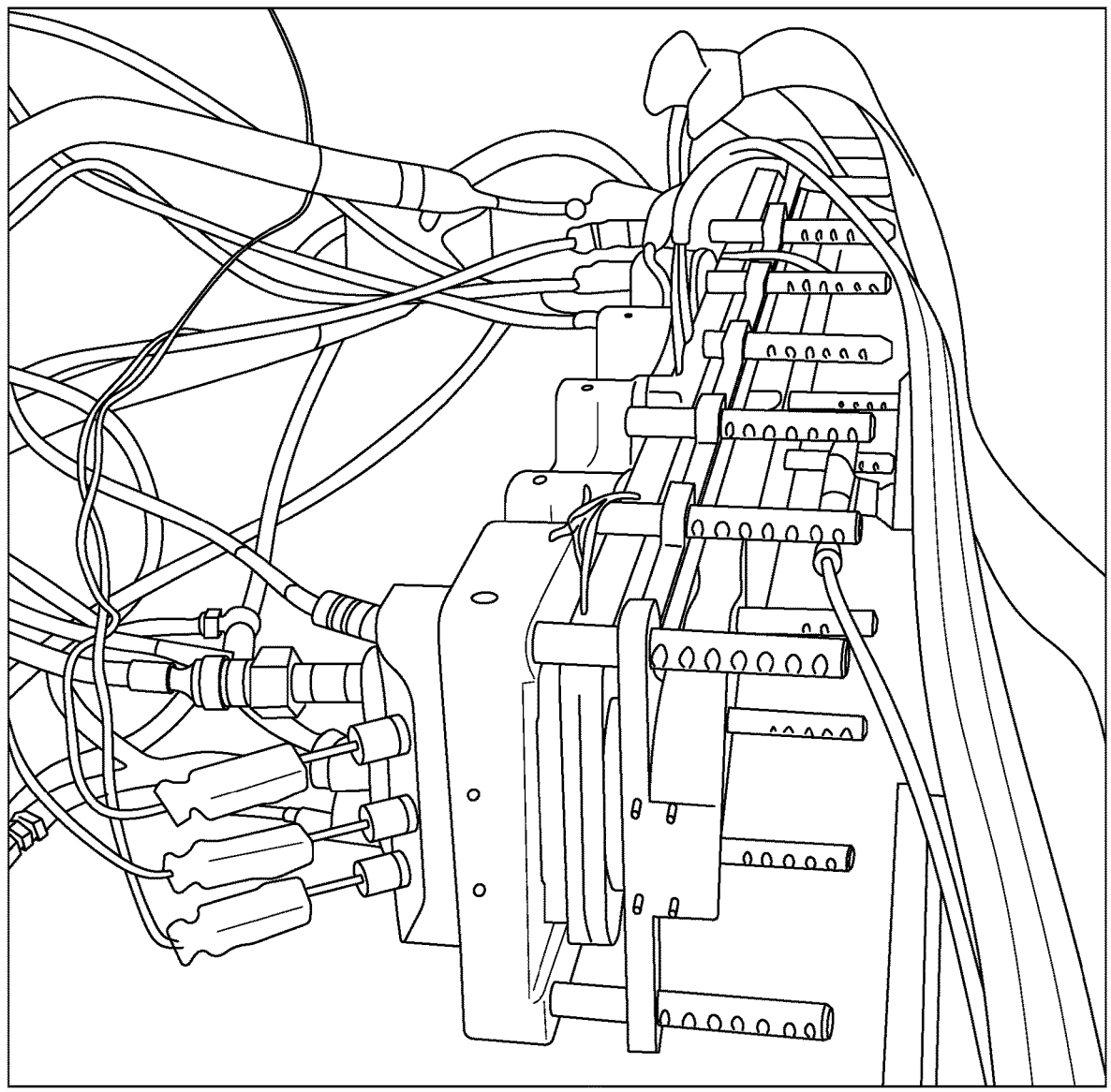
FIG. 4 is a fuel cell stack.

The word "diagnostic" usually implies detection, isolation and identification of faults. Hydrogen crossover leaks at different rates in automotive PEM cells are detectable by using electrochemical impedance spectroscopy (EIS). The methods and devices disclosed herein include the use of EIS to detect a leak in a stack with a large number of PEM fuel cells. As no hydrogen was detected downstream of the stack, for the purposes of the present methods and devices the assumption was made that hydrogen crossing over was typically totally recombined with oxygen throughout the MEA length. Such recombination would also produce extra water that could result in full or partial self-sealing of the pinholes (see, e.g., Stefan Kreitmeier, Matteo Michiardi, Alexander Wokaun, Felix N. Buchi, "Factors determining the gas crossover through pinholes in polymer electrolyte fuel cell membrane", Electrochimica Acta 80: 240-247, 2012). To account for the effect of extra water resulting from the leak, the leak rate during operation of the fuel cell stack was estimated using neural networks (NNs).

In accordance with the methods and devices disclosed herein, neural networks and EIS impedance measurements are used to calculate hydrogen leak rates. Neural networks are in fault diagnostic (see, e.g., N. Yousfi-Steiner, D. Candusso, D. Hissel, Ph. Mocoteguy, "Model-based diagnosis for proton exchange membrane fuel cells", Mathematics and Computers in Simulation 81: 158-170, 2010; Justo Lobato, Pablo Canizares, Manuel A. Rodrigo, Jose J. Linares, Ciprian-George Piuleac, Silvia Curteanu, "The neural networks based modeling of a polybenzimidazole-based polymer electrolyte membrane fuel cell: Effect of temperature", Journal of Power Sources 192: 190-194, 2009), to represent the complex behavior of the fuel cell system without the need of deriving a mathematical model. Due to consistent patterns of impedance signatures and a large set of data being entered into the neural network, the effect of leak rate on the fuel cell system could be taken into consideration without the need of prior knowledge to the interior mass and heat transfer encountered.

Overview of EIS

Electrochemical impedance spectroscopy (EIS) is an experimental technique that can be used to perform impedance measurements over a wide frequency range for DC power generation devices. The main advantage of EIS is the possibility to resolve, in the frequency domain, the individual contributions that affect the overall PEM fuel cell performance under load conditions (C. Brunetto, A. Moschetto, G. Tina, Electr. Power Syst. Res. 79: 17-26, 2009). The effect of hydrogen leaks on a single cell can be evaluated using an EIS method. In order to establish impedance behavior at different hydrogen leak rates, the impedance signatures of reduced oxygen concentrations in the cathode are compared with and thus mapped to impedance signatures of the hydrogen leaks. These faulted impedance signatures are then used to detect reverse potential faults in a stack or the outcomes thereof.

EIS usually employs a frequency response analyzer (FRA) to apply either a small AC voltage or current perturbation signal to a cell, and measures its output signal for a wide frequency range. The impedance is calculated by dividing the voltage by current, in the form of a magnitude and phase angle, at each specific frequency. Impedance spectroscopy has the ability to characterize many of the electrical properties of materials and their interfaces with electrodes. This ability has made the EIS technique widely used in modeling and diagnostics of PEM fuel cells, where individual contributions affecting cell performance can be distinguished by fitting the impedance spectrum into parameters of an equivalent circuit model. Electrical circuits with different configurations, components, and degree of complexity have been proposed in the literature.

The basic equivalent circuit often used to represent fuel cell operation is the Randles circuit shown in FIG. 1, where $C_{dl}$ is the double layer capacitance of the catalyst surface, $R_{HF}$ describes the movement within a conducting media and illustrates the sum of contribution from contact resistance between components and high frequency resistance of the cell components, and $R_{ct}$ is the resistance that occurs when electrons transfer at the electrode/electrolyte interface. $R_{ct}$ decreases when overpotential increases due to the faster oxygen reaction rate. Kang et al. (J. Kang, D. W. Jung, S. Park, J. Lee, J. Ko, J. Kim, Int. J. Hydrog. Energy, 35: 3727-3735, 2010) noticed an increase in $R_{ct}$ with increasing the degree of the reverse potential fault in a fuel cell caused by fuel starvation. Nyquist plots show the resistance versus reactance at multiple frequencies, as obtained by the EIS measurements, FIG. 2. The high frequency region of the impedance spectrum represents the high frequency resistance whereas the low frequency region represents the high frequency resistance and charge transfer resistance respectively (X. Yuan, C. Song, H Wang, J. Zhang, Electrochemical Impedance Spectroscopy in PEM Fuel Cells, Fundamentals and Applications, Springer-Verlag, London, 2010). At high frequency, the $C_{dl}$ is short circuited and the $R_{HF}$ is measured. As frequency decreases, the impedance becomes a combination of resistance and reactance from the capacitive element. At low frequency, $C_{dl}$ acts like a blocking diode and the total resistance is equal to $R_{HF}$ and $R_{ct}$.

Electrical Circuit Model:

More complicated circuits than the Randles circuit are proposed in the literature for different purposes. Others (C. Brunetto, A. Moschetto, G. Tina, Electr. Power Syst. Res. 79: 17-26, 2009; M. Ciureanu, R. Roberge, J. Phys. Chem. 105: 3531-3539, 2001; J. Kawaji, S. Suzuki, Y. Takamori, T. Mizukami, M. Morishima, J. Electrochem. Soc. 158: 1042-1049, 2011) have added additional components to the Randles circuit to include mass transfer effects. Series connections represent subsequent events while parallel connections represent simultaneous events Makharia et al. (R. Makharia, M. F. Mathias, D. R. Baker, J. Electrochem. Soc. 152: 970-977, 2005) used a transmission line circuit to include the catalyst layer resistance. Cano-Castillo et al. [U. Cano-Castillo, A. Ortiz, S. Cruz, L. G. Arriaga, G. Orozco, J. Electrochem. Soc. 3: 931-939, 2006, compared the transmission line circuit with a circuit similar to the ones in which a resistive and capacitive element similar to the Randles circuit (C. Brunetto, A. Moschetto, G. Tina, Electr. Power Syst. Res. 79: 17-26, 2009; M. Ciureanu, R. Roberge, J. Phys. Chem. 105: 3531-3539, 2001). Both the transmission line and the modified Randles circuit gave reasonable fit with the experimental data.

Andreasen et al. (S. J. Andreasen, J. L. Jespersen, E. Schaltz, S. K. Kær, Fuel Cells 09 4: 463-473, 2009) used two circuits, the modified Randles circuit described above, and the other with a constant phase element (CPE) instead of a capacitor in the second circuit. The authors showed that using the circuit with the CPE better fit their impedance data. Others (X. Yuan, J. C. Sun, M. Blanco, H. Wang, J. Zhang, D. P. Wilkinson, J. Power Sources 161: 920-928, 2006; A. M. Dhirde, N. V. Dale, H. Salehfar, M. D. Mann, T. Han, IEEE Transactions on Energy Conyers. 25; 3, 2010; J. Lebæk Jespersen, E. Schaltz, S. K. Kær, J. Power Sources 191: 289-296, 2009) also replaced capacitive elements with CEPs to adapt their models with the deformed impedance arc. This deformation results from the porous structure of the electrodes where the electron charges are not distributed evenly inside the electrode.

Another equivalent circuit variant (S. Rodat, S. Sailler, F. Druart, P.-X. Thivel, Y. Bultel, P. Ozil, J. App. Electrochem. 40: 911-920, 2010) represented the mass transport phenomena with a Warburg impedance element in series with the Randles circuit. In this study it was sufficient to represent the impedance spectra with the modified Randles equivalent circuit shown in FIG. 3, utilizing resistive and capacitive elements to describe both kinetic and mass transport phenomenon. More specifically, $R_{mt}$ describes the oxygen diffusion resistance, while C has been used to describe the diffusion layer in the Pt/C agglomerate structure where oxygen is consumed at the Pt surface (J. Kawaji, S. Suzuki, Y. Takamori, T. Mizukami, M. Morishima, J. Electrochem. Soc. 158: 1042-1049, 2011). Those parameters represent the cathode side of the cell where oxygen reduction rate (ORR) at the cathode is several orders of magnitude slower than the hydrogen oxidation rate (HOR) (N. Yousfi-Steiner, Ph. Mocoteguy, D. Candusso, D. Hissel, A. Hernandez, A. Aslanides, J. Power Sources 183: 260-274, 2008).

EXPERIMENTAL SETUP

Full-size FCvelocity™-1100 fuel cells were tested at 20 and 50 A loads. The experiments were conducted for a stack with small, medium and large leak rates at the inlet side of the leaky cell, with a differential pressure (differential pressure) of 2, 4, 6 and 8 psi (13.8, 27.6, 41.4 and 55.2 kPa) using air as oxidant. The leaky cell in each stack was placed between normal cells. The normal and leaky cells were also tested with different oxygen concentrations; see FIG. 21.

Reactant and oxidant flow rates were proportional to the number of cells in the stack. Oxygen concentration was reduced gradually by controlling the mixture of nitrogen and oxygen at the cathode side. The oxidant flow rate was kept constant to isolate and minimize the effect of water accumulation on the impedance signatures.

To separate the single contributions of the performance loss of the fuel cell during load, impedance measurements can be conducted while changing only one variable at a time. All EIS test were made at low currents; 20 A and 50 A to ensure that hydrogen leak was not hindered by the increasing content of water resulted from higher ORR at higher loads. Running at low loads ensures an adequate hydration on the anode and cathode where water diffuses between those two compartments. This ensured that cathodic overpotential was the main contribution to the impedance signature. At higher current densities, the anode tends to dry out as a result of higher proton migration to cathode carrying water molecules. This adds an anodic overpotential contribution to the impedance spectra. To allow a fair comparison between the impedance of leaky cells and the normal cell, hydrogen leakage across the leaky cells was minimized by keeping 0 differential pressure across the holes. All measurements were conducted using Kikusui EIS equipment in galvanostatic mode with a 10% AC amplitude over the frequency range 20 k-80 m Hz. EIS measurements were conducted once the stack reached equilibrium for each operating condition tested. In order to avoid the change in current and voltage relationship during measurements, the total frequency sweep of the impedance measurement were conducted in the shortest length of time possible, about 6 minutes. The system was therefore assumed to be at a steady-state condition during the measurement. To avoid frequency interference, the power supply and loadbank (see FIG. 5) were turned off while measuring the impedance.

Prior to testing, leak rates were evaluated at 0.5 bar (50 kPa) air pressure across the MEA. The MEA was then placed in an open-faced fixture with 3 to 5 psi differential pressure (20.7-34.5 kPa) differential pressure to identify the holes' location. Submerged in deionized (DI) water, bubbles appear at the surface of the MEA revealing the location of the leaks.

In testing, temperatures of the anode and cathode are kept equivalent by providing similar coolant flows through the stack. The cell voltage was recorded between the terminals of the stack, which is shown in FIG. 4. The fuel cell stack in FIG. 4 includes a plurality of plates, such as an anode plate and a cathode plate. Each of the plates may have a rectangular shape. The rectangular shape is generally consistent throughout the plates to form the fuel cell stack having generally the same rectangular shape.

The test bed used a TDI—Dynaload loadbank RBL488 400-600-4000 and Xantrex DC power supply XPR 10-600 connected in series to satisfy the voltage limitation of the loadbank. The Kikusui EIS equipment consisted of an FC impedance meter KFM2150 and three electronic loads PLZ664WA. The loadbank and power supply were connected to the fuel cell and EIS machines in parallel, as shown in FIG. 5. This configuration provided the required load by using either the EIS equipment or the test station loadbank between test periods. The power supply was used to overcome voltage limitations of the loadbank when higher voltage was needed for higher current testing.

The test bed controlled and monitored the stack temperature, fuel and air humidity, gas flow rates, pressures, and load current. Two mass flow controllers (MFC) for oxidant and fuel were installed in the test bed to allow low and high flow rates. Gas mixers were used in this experiment to control the oxygen and hydrogen concentrations balanced with nitrogen. The use of mixers allowed the testing of various oxygen and hydrogen concentrations while maintaining constant flow rates, FIG. 22. Using constant flows made the EIS measurements more stable due to improved water management.

To check with the neural network estimation, the impedance of known amounts of hydrogen directly injected to the cathode side of a single cell was measured. The hydrogen was injected by adding hydrogen injection MFCs to the experimental setup, as shown schematically in FIG. 6. While only one hydrogen injection MFC is shown in FIG. 6, two injection MFCs were used in this experiment, one with a maximum range of 200, and another with a maximum range of 2000 cm3 min$^{-1}$ (ccm), respectively. To minimize the leak through the pinholes, the pressure across the MEA anode and cathode inlet can initially be kept at 0 psi. Impedances were measured at 20 and 50 A loads.

Diagnostic Method

Two sets of data are obtained with stack sizes of 5, 9 and 19 cells. The first set of data was measured at reduced oxygen concentration rates on the cathode side while keeping the differential pressure (dP) across the membrane at the inlet of the stack at 0 psi. The second set of data was measured at increased differential pressure between anode and cathode while keeping oxygen concentration in air at normal level; i.e. 21%. The two impedance data sets are interrelated by the recombination of oxygen with the leaking hydrogen through the pinholes. However, oxygen concentration impedance was obtained by an equal reduction of oxygen in all cells whereas the differential pressure impedance was obtained by the reduction of oxygen at the leaky cell in the n-cells stack.

In order to identify the amount of hydrogen leak at the stack without measuring it directly, neural network was used to map oxygen concentration impedance data with differential pressure impedance data. Mapping was accomplished by training the network using oxygen concentration impedance with its associated concentrations, as shown in FIG. 7.

Hydrogen Leak Rate

With the increasing amount of differential pressure at the inlet of the MEA, hydrogen leak increases through the pinholes. As there was no access to the upstream of the MEA where the pinholes are, the leak rate was estimated by using oxygen concentrations simulated by the neural network at different differential pressures. Oxygen stoich (utilization) was calculated by using the following equation:

$$lambda_{O2} = \frac{provided}{consumption} = \frac{flow \cdot O_2 \% \cdot N}{C \cdot I \cdot 0.2095 \cdot N} \quad (1)$$

where:
lambda$_{O2}$ is 4.7 and 4.02 for 20 and 50 A respectively
flow is air flow rate of a single cell [SLPM]
O$_2$% is percentage of oxygen concentration in air
C is air consumption, 0.0167 [SLPM/A/cell]
I is load [A]
N is number of cells in the stack
The oxygen left in the cathode after consumption for a single cell is:

$$O_{2L} = [flow \cdot O_2] - [0.0167 \cdot I \cdot 0.2095] \quad (2)$$

The change in impedance signatures due to the reduction of oxygen concentrations was linked to the percentages of $O_{2L}$ using neural network. Simulating the amount of recombined oxygen at different differential pressures, it was found that the amount of oxygen used in the electrochemical reaction could be calculated by subtracting $O_{2L}$ flow from the regular amount of oxygen in the air flow. Then the current resulted from the consumption of oxygen at the cathode could be calculated. Subtracting the current at 0 differential pressure from the current at higher leak rates, the leak current could be derived. This current was then used in estimating the consumed hydrogen due to leak by:

$$Q_{H2} = I_{leak} \cdot 0.0069478 \cdot lamda_{H2} \qquad (3)$$

Neural Network

Artificial neural networks include statistical learning algorithms that are derived the study of biological neural networks. These neural networks are adaptive in nature, can be used for pattern recognition, and can be configured to approximate complex nonlinear functions using a number of "neurons" ordered in layers and connected to each other by weights. Weights are optimally adjusted to map an input/output (or target) relationship in a process called training where all possible operating conditions are illustrated by the network. Training can be made either by using data available beforehand (supervised learning) or in the absence of pre-available data in what is called (unsupervised learning). Once the relationship between input/output is established, the weights are fixed and the network is able to predict outputs from a new set of inputs.

Among various neural network models, the feed-forward neural network structure is widely used in literature. Other neural network models are proposed in the literature (Chen Changzheng and Mo Changtao, "A method for intelligent fault diagnosis of rotating machinery", Digital Signal Processing 14: 203-217, 2004; Wu Jian-Da, Liu Chiu-Hong, "An expert system for fault diagnosis in internal combustion engines using wavelet packet transform and neural network", Expert Systems with Applications 36: 4278-4286, 2009; Shaoduan Ou, Luke E. K. Achenie, "A hybrid neural network model for PEM fuel cells", Journal of Power Sources 140: 319-330, 2005). However, Lobato et al. (Justo Lobato, Pablo Canizares, Manuel A. Rodrigo, Jose J. Linares, Ciprian-George Piuleac, Silvia Curteanu, "The neural networks based modeling of a polybenzimidazole-based polymer electrolyte membrane fuel cell: Effect of temperature", Journal of Power Sources 192: 190-194, 2009) found that multilayer feed-forward gave the best performance when compared with other networks. A special feed-forward neural network training algorithm is the multilayer back propagation (BP) algorithm that is commonly used for pattern recognition and classification, and hence for machine fault diagnosis (Andrew K. S. Jardine, Daming Lin and Dragan Banjevic, "A review on machinery diagnostics and prognostics implementing condition-based maintenance", Mechanical Systems and Signal Processing 20 12(6): 1483-1510, 2006). Back propagation uses a set of input and output data to update the weights of the network in forward and backward directions until the error between the output and target reaches it threshold limits. Steiner et al. (N. Yousfi Steiner, D. Hissel, Ph. Mocoteguy, D. Candusso, "Diagnosis of polymer electrolyte fuel cells failure modes (flooding and drying out) by neural network modeling", International journal of hydrogen energy (2010), doi:10.1016/j.i-jhydene.2010.10.077] used the back propagation technique in diagnostic of a PEM fuel cell.

The neuron output y can be described by:

$$y = f\left(\sum_{j=1}^{N} w_j x_j + b\right) \qquad (4)$$

where the input signal $x_j$ is multiplied by the weight $w_j$ that is randomly selected and b is the bias input to the neuron. After summing the inputs from other nodes, the output signal of the neuron is obtained by applying an activation function $f$ to the result. The back propagation training algorithm uses a least square function to minimize error E(w) between the output of the network $y_k^i$ and its corresponding targets $t_k^j$ by adjusting the network weights.

$$E(w) = \frac{1}{2} \sum_{j=1}^{N} \sum_{k=1}^{M} (t_k^j - y_k^j)^2 \qquad (5)$$

Electrochemical impedance spectroscopy (EIS) can detect crossover leaks of various sizes in fuel cell stacks. The impedance signatures are proportional to the amount of leak and number of cells in the stack. The impedance signatures are compared with impedance signatures of test stacks that have no leaks at reduced oxygen concentrations. The impedance signatures are also compared to impedance signatures of test stacks with some leaks. The neural network method can then be used to quantify the amount of recombined oxygen at the leaky cell. Using the impedance signatures of leaky stacks, the network is able to simulate a reduced amount of oxygen due to leaks. This network output is then used to back calculate the amount of hydrogen leak in the stack.

For example, there may be a first test stack that has no leaks. The test stack may have a plurality of plates that have the same rectangular shape as the fuel cell stack described above. There may also be a second test stack that has a leak in at least one of the cells. The second stack may also have a plurality of plates where each plate has the same rectangular shape of the fuel cell stack.

Impedance Signature

Impedance signatures increase with decreasing amounts of oxygen concentration. This pattern is consistent with the decreased amount of oxygen at different stack sizes, see FIGS. 8a and 8b, where FIG. 8a is oxygen concentration impedance signatures with a 20 A load of a smaller number of fuel cells, such as 5 fuel cells and FIG. 8b is oxygen concentration impedance signatures with a 20 A load of a larger number of fuel cells, such as 9 fuel cells. However, when the amount of oxygen is insufficient to deliver enough power to the stack, the impedance increases sharply, as shown in FIG. 8b.

Similar behavior occurs with increasing differential pressure across the MEAs, where impedance signatures increased. The increase in impedance was due to the recombination of oxygen at the cathode due to leak. However, with an increasing amount of leak, the impedance signature reduced, see FIGS. 9a and 9b, where FIG. 9a is impedance of a 5-cell stack at 20 A with a medium leaky cell and FIG. 9b is impedance of a 5-cell stack at 20 A with a large leaky cell. This reduction in impedance is due to the loss of power of the leaky cell in the stack. In other words, the leaky cell was not contributing to the stack impedance at high differential pressures. With further increase in leak rates, impedance is saturated and no reduction in the signatures is noticed. The increase in impedance signatures is significant with the smaller sized stacks, especially with the large leaky cell, see FIG. 9b. With the increase of stack size, the significance of signatures is reduced, see FIG. 10, which includes differential pressure impedance of a much larger fuel cell stack, such as a 19-cell stack with 20 A load with a large leaky cell. Similar impedance behavior can also occur at higher loads.

Impedance signatures show a clear relation between oxygen consumption and hydrogen leaks. However, impedance signatures alone cannot be used to quantify leak rates. Thus, neural network are used to quantify the recombined amount of oxygen in the cathode due to leak.

Neural Network Simulation

A study by Hsueh (K. L. Hsueh, "A Study of Artificial Neural Networks for Electrochemical Data Analysis", ECS Transactions 25(28): 47-58, 2010) used the absolute value and phase angle of the impedance signatures in training the neural network. In contrast, this method uses the imaginary and real parts of the impedance in training the network, see FIG. 11. The training signatures contain 112 impedance values measured at the range of 1260 to 0.156 Hz. Several trials can result in training the feed-forward network, until a proper network structure is achieved—including size of data, number of hidden layers, and number of neurons. Generally, one can expect that the larger the training data, the better the conversion of the network.

The training can be performed with 144 impedance data of the stack sizes 5, 9 and 19 cells and 20 neurons in the hidden layer. Experiments may be conducted for stacks with no leaks and stacks with small to medium sized leaks at 20 and 50 A loads for training the neural network. The network targets are: number of cells in the stack, load, and the percentage of oxygen concentration left in the cathode after consumption, as shown in FIG. 23. In training the network MATLAB 7.5 can be used with Levenberg-Marquardt backpropagation function (trainlm) optimization algorithm that is usually best suited for function approximation problems. The network can be trained until the square of error reached is just below 0.01.

Hydrogen Leak Rate

Estimated Leak Rate

Figure 12:
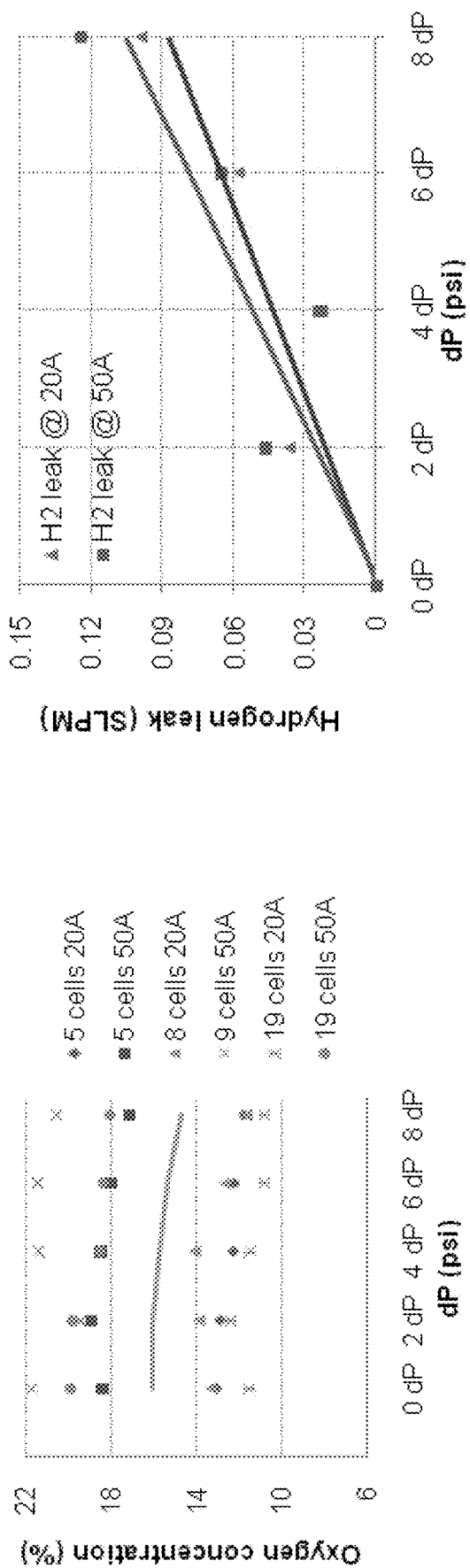
FIG. 12 includes graphs of oxygen concentration and hydrogen leak rates for a small leaky cell in a cell stack having a number of cells.
Figure 13:
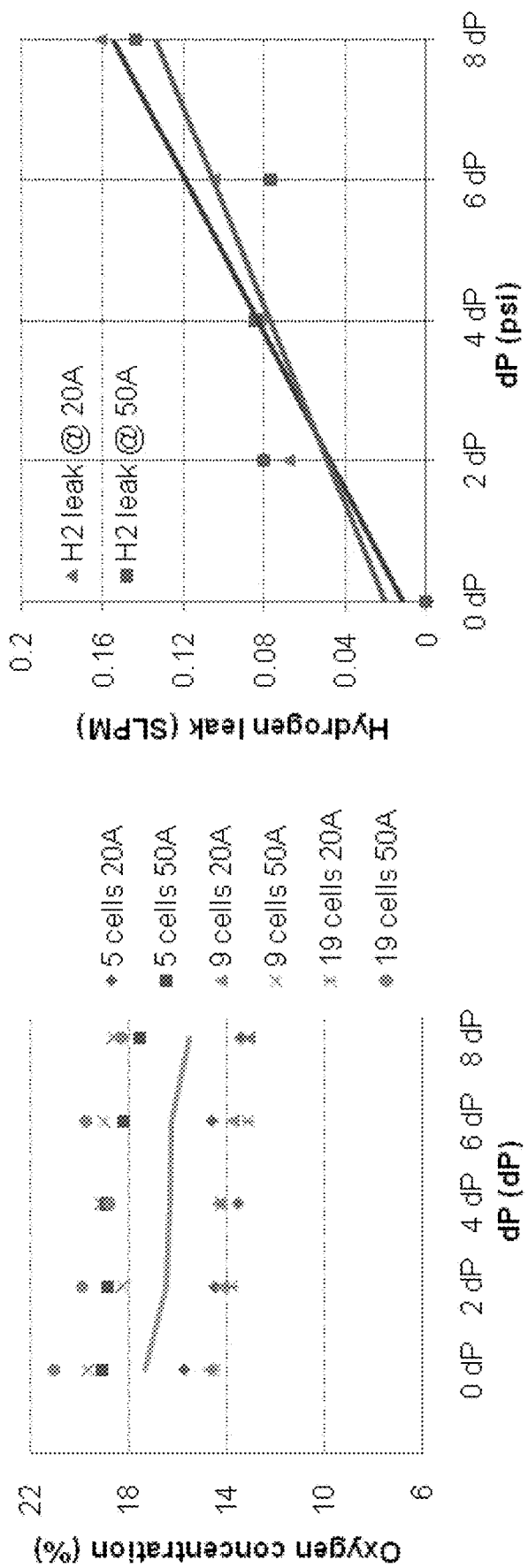
FIG. 13 includes graphs of oxygen concentration and hydrogen leak of a medium leaky cell in a cell stack having a number of cells.
Figure 14:
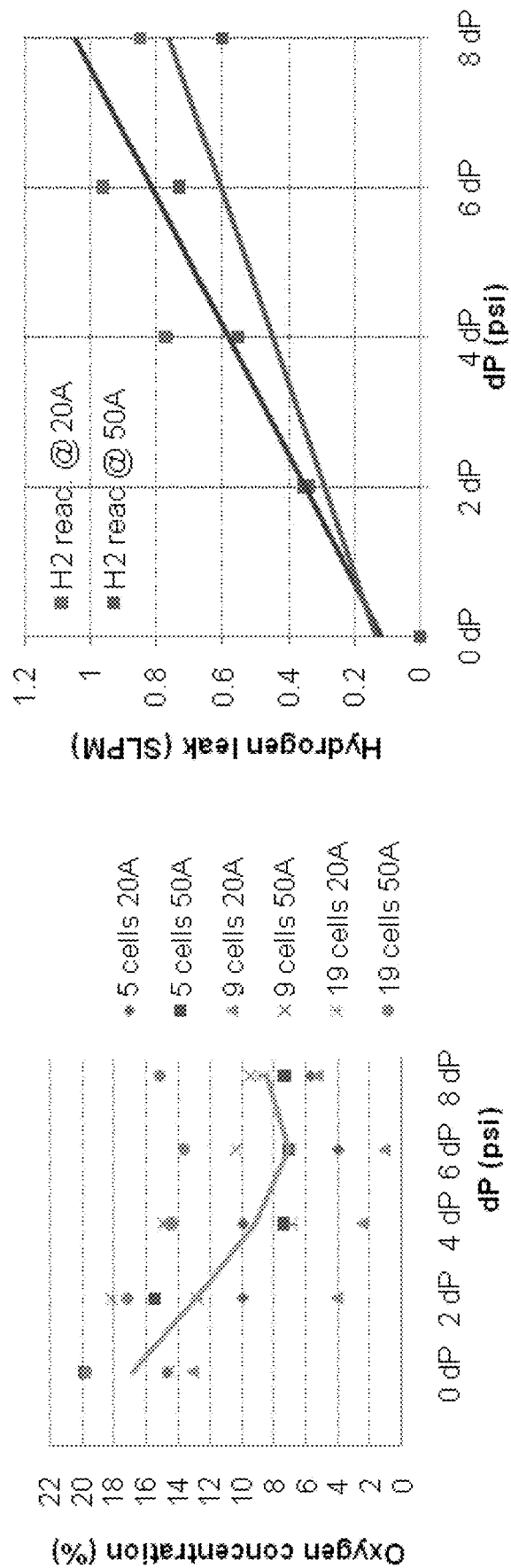
FIG. 14 includes graphs of oxygen concentration and hydrogen leak rates of a large leaky cell in a cell stack having a number of cells.

After training the neural network, the network simulates differential pressure impedance data. The oxygen concentrations resulting from the simulation are then used in calculating the hydrogen leaks at different stack sizes. Using the average oxygen concentration in 20 A and 50 A loads, hydrogen leaks in the small, medium and large leaky cells are estimated. The estimated leak rates are proportional to the size of measured ex-situ leak rates of the leaky cells (measured with air). For the small leaky cell, a small drop in oxygen concentration is detectable over the range of differential pressures. This drop represents the small number of hydrogen leak rates at 20 A and 50 A loads, see FIG. 12, which includes graphs of oxygen concentration and hydrogen leak rates for a small leaky cell in a cell stack having a number of cells. A larger drop for the medium leaky cell is detected, see FIG. 13, which includes graphs of oxygen concentration and hydrogen leak of a medium leaky cell in a cell stack having a number of cells. For a large leaky cell, the concentration drop is significant with the increase of differential pressure. This drop is reflected in the increasing of leak rates at higher differential pressures, see FIG. 14, which includes graphs of oxygen concentration and hydrogen leak rates of a large leaky cell in a cell stack having a number of cells.

Neural network simulation shows a continuous reduction in oxygen concentration with the increasing of differential pressure. This agrees with the observation that the reduction of impedance at higher differential pressure is the result of loss in the leaky cell due to the loss of sufficient amounts of oxygen. The continuous reduction in concentration gives a clear indication that the network was able to learn the correct behavior of the impedance. However, the hydrogen leak estimation is less than the off-line ex-situ measured leak rates, which may be attributable to an excess amount of water in the cathode due to recombination partially sealing the leak.

Measured Leak Rate

Figure 15:
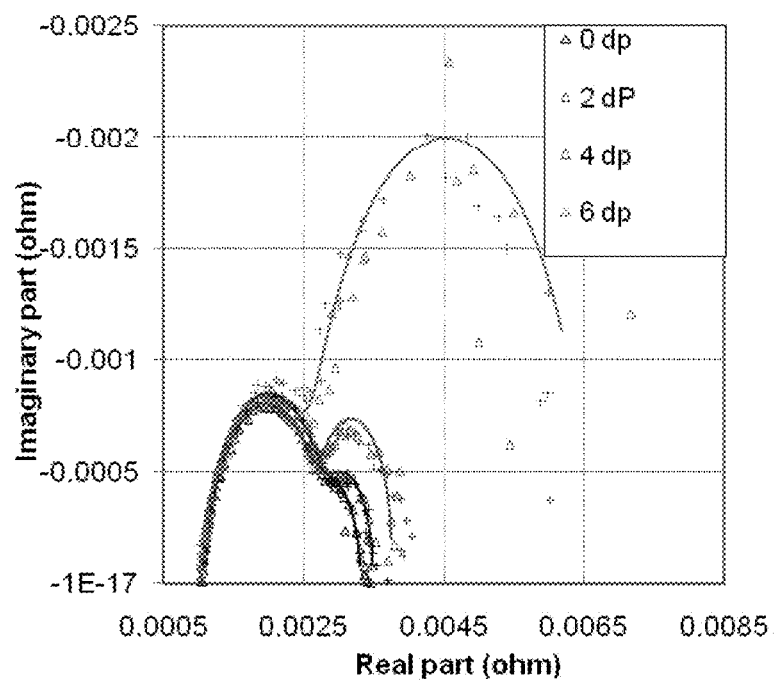
FIG. 15 is a graph of differential pressure impedance of a single cell with injected hydrogen.
Figure 16:
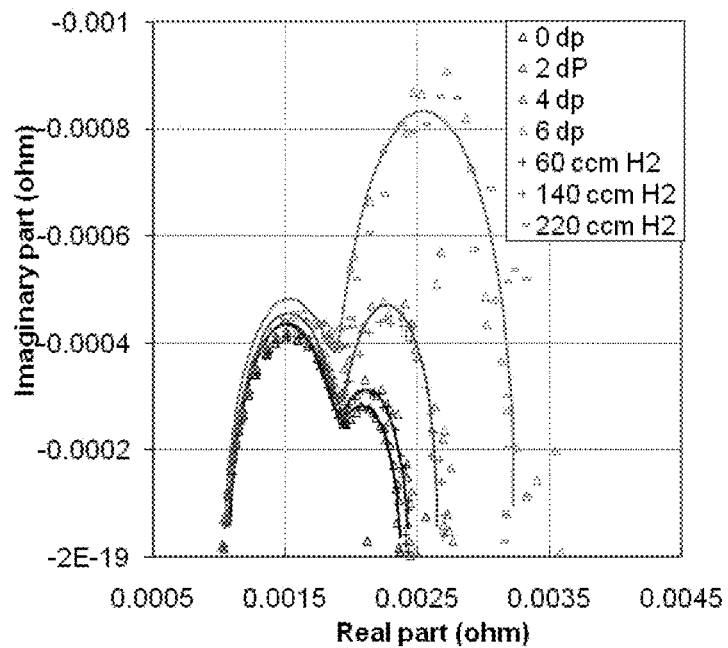
FIG. 16 is a graph of differential pressure impedance of a single cell with injected hydrogen.

While keeping differential pressure across the medium leaky fuel cell at 0 psi, hydrogen is injected at the cathode side during operation. Impedance of the injected hydrogen at 0 differential pressure is compared with the impedance of the same cell with no injection at higher differential pressure levels. Comparing the matching impedance, the amount of hydrogen leaked through the MEA can be determined, such as through experimentally quantification, see FIG. 15, which is a graph of differential pressure impedance of a single cell with injected hydrogen at 20 A load. The solid lines are used to fit data of matched impedance signatures. Impedance signatures at 8 differential pressures are distracted due to the insufficient voltage produced by the cell. Leak rates at a higher load are slightly higher than the rates at a lower load, see FIG. 16, which is a graph of differential pressure impedance of a single cell with injected hydrogen at a 50 A load. Although the water production at 50 A is higher, the reason for the higher amounts of leak rates is due to the higher flow rate of hydrogen, namely 1.42 and 0.66 SLPM for 50 A and 20 A loads, respectively.

Figure 17:
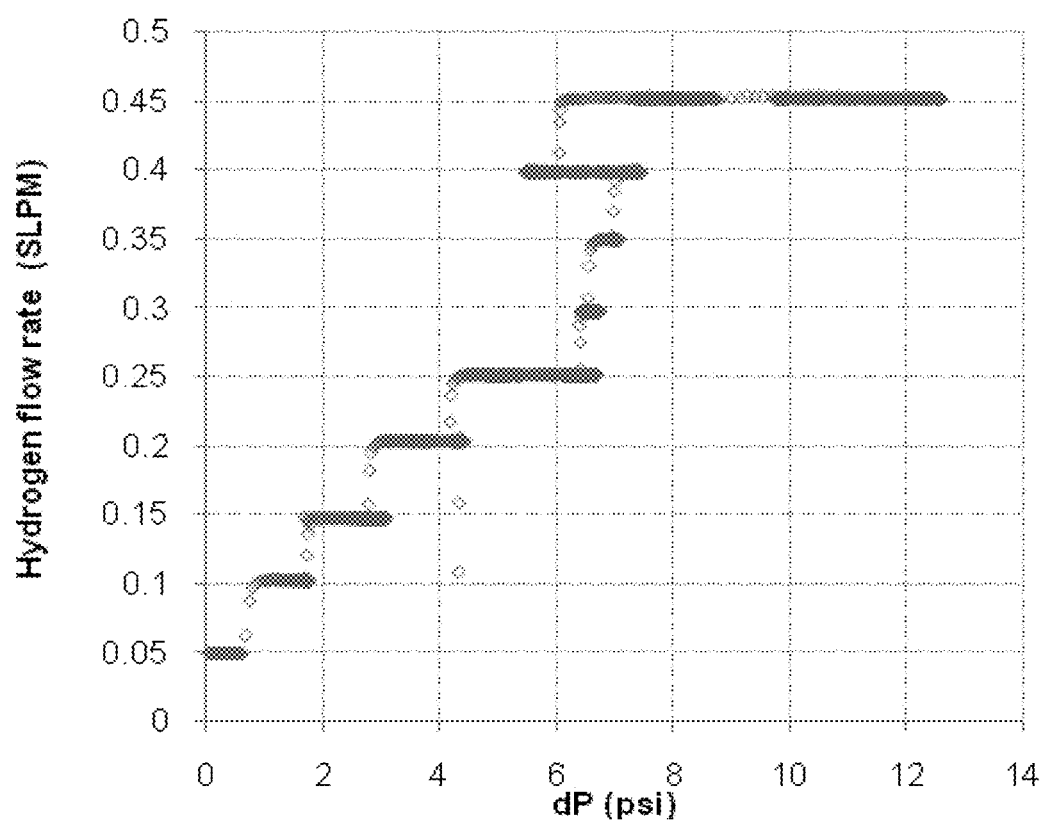
FIG. 17 is a graph of differential pressure versus hydrogen leak rates of a medium leaky cell during off line testing.
Figure 18:
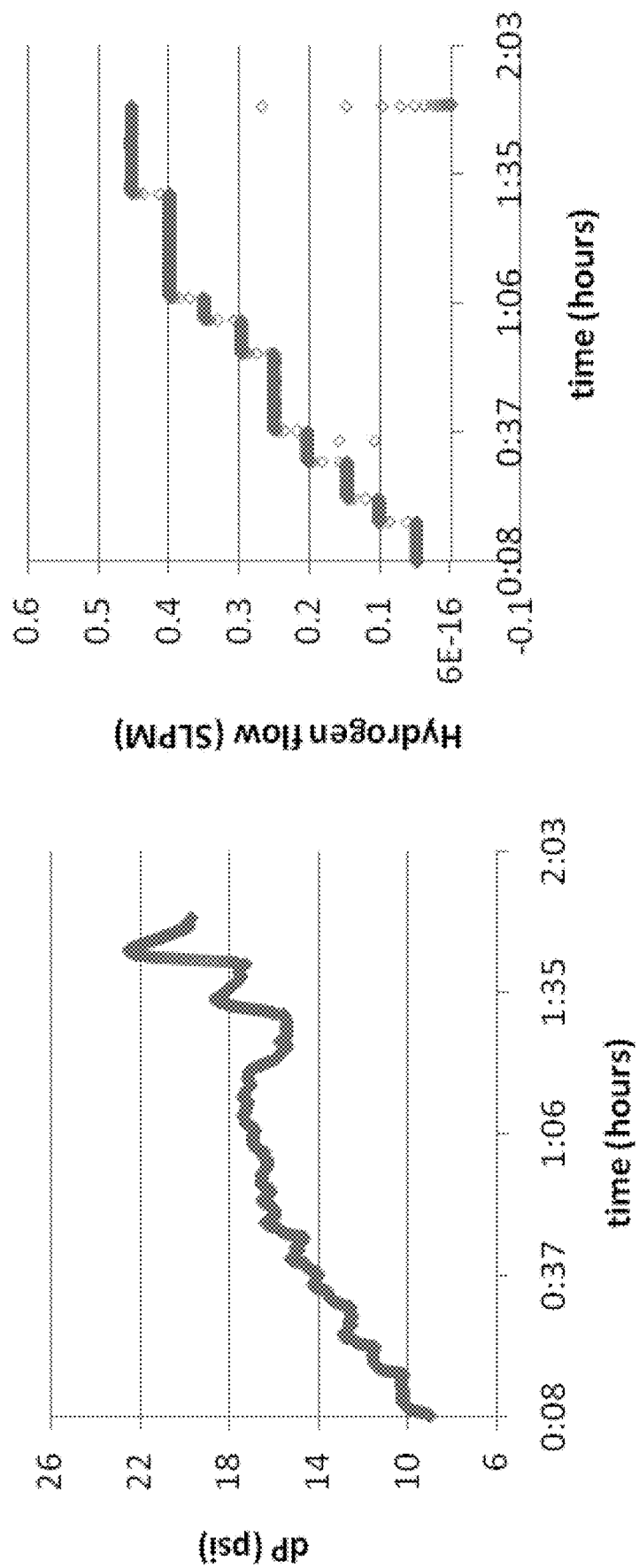
FIG. 18 includes graphs of differential pressure versus time and hydrogen flow versus time.

The effect of water production on leak rate during operation can be analyzed by testing the amount of hydrogen leak rate off-line in a single leaky-cell test at open circuit voltage (OCV). In order to eliminate recombination of the leaked hydrogen with oxygen, nitrogen is used instead of air in the cathode side. In this off-line test, the hydrogen flow rate is increased slowly while the anode outlet shut-off valve (see FIG. 6) is closed. In this configuration, the hydrogen entering the anode has nowhere to go except through the membranes of the good (leak free) cells and (mostly) through the pinhole of the leaky-cell, where increasing the hydrogen flow at the anode side, increases the differential pressure through the inlet of the MEA, which is measured as shown in FIG. 17, which includes a graph of differential pressure versus hydrogen leak rates of a medium leaky cell during off line testing. To reduce the condensation at the stack, the medium leaky cell was placed in between two normal MEAs. As it can be noticed from the figure, the differential pressure of the anode above the cathode was increasing steadily while increasing the flow rate. However, between 6 and 8 psi differential pressure the flow can be hindered due to the condensation of water in the stack. This drop in differential pressure can be noticed between 1:15 to 1:30 hours where resistance to the flow was not corresponding to the increase in the hydrogen leak rate, see FIG. 18, which includes graphs of differential pressure versus time and hydrogen flow versus time.

Comparing the leak rate during operation at 20 A load and during off-line, the effect of recombination is established, see FIG. 19, which is a graph of measured and estimated hydrogen leak rates. The maximum leak rate measured during the off-line mode, and the estimated leak rate is closer to the on-line leak rate. Error between estimated and on-line leak rates was negligible at 2 psi differential pressure, and somewhat higher at higher differential pressure. However, as anode pressure is typically kept a little higher than the cathode pressure in most systems, any error between estimated leak rates and on-line leak rates would be negligible, rendering this method suitable for the diagnostic criteria needed for most fuel cell stacks.

The methods disclosed herein employ neural networks and EIS to detect and quantify hydrogen leaks in PEM fuel cell stacks. EIS was used to measure the impedance of oxygen concentration and differential pressure at different stack sizes. As increasing differential pressure resulted in more hydrogen leak and less oxygen concentration in the cathode, the amount of hydrogen leak in the n-cells stack was established using neural network. The network training was conducted using the impedance data of a particular stack size or a particular leak rate. The network simulation was then used in calculating the hydrogen leak rate in the stack.

Using these diagnostic methods, the leak rate of the impedance signature was estimated effectively during operation of the fuel cell system. This estimation may differ from the off-line ex-situ leak measurements, likely because of the existence of water produced in operation blocking or partially-blocking the pinholes. At lower differential pressures, the on-line and estimated leak rates are almost identical, while at higher differential pressures the off-line measured leak rates are typically higher. Despite the variance between estimated and measured leak rates, the methods disclosed herein are appropriate to most fuel cell systems as they typically keep differential pressures across MEAs small.

FIG. 20 is a schematic diagram of a fuel cell diagnostic apparatus. The apparatus includes an analyzer that is coupled to an operational fuel cell stack. The analyzer can provide signals to the fuel cell stack and can receive measurements from the fuel cell stack. In one embodiment, the analyzer is also coupled to a first test stack and a second test stack, where the analyzer can send and receive information from the first and second test stacks, see the solid line arrows between these elements. The analyzer is configured to receive the impedance signatures from the first test stack associated with oxygen concentration, where the first test stack is free of any leaky cells. The analyzer is configured to receive impedance signatures of differential pressure associated with hydrogen and oxygen in the second test stack. The second test stack includes at least one leaky cell in the plurality of cells in the stack. The analyzer is coupled to a neural network and is configured to provide the impedance signatures from the first and second test stacks to the neural network. The neural network can then map the impedance signatures of the first test stack to the correspondence impedance signatures of the second stack. The neural network also receives impedance signatures from the operational fuel cell stack based on a signal provided by the analyzer to the operational fuel cell stack. Once the neural network is trained, the neural network can provide a hydrogen leak rate of the operational fuel cell stack based on the various impedance signatures collected and processed by the neural network. In another embodiment, the first test stack and the second test stack can be coupled directly to a neural network to receive the impedance signatures from the first test stack and the second test stack, see the dashed lines.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method, comprising:
   determining a hydrogen leak rate in a polymer electrolyte membrane fuel cell stack, the determining including:
   generating a first set of data points for impedance signatures of oxygen concentrations in a first fuel cell test stack, the first fuel cell test stack having no internally leaky cells;
   generating a second set of data points for impedance signatures of differential pressures of hydrogen and oxygen in a second fuel cell test stack, the second fuel cell test stack having at least one internally leaky cell;
   mapping the impedance signatures of the oxygen concentrations from the first set of data points to the impedance signatures of the differential pressures of hydrogen and oxygen from the second set of data points;
   passing an AC signal through the fuel cell stack;
   detecting impedance signatures from the AC signal in the fuel cell stack;
   identifying an oxygen concentration of the fuel cell stack by matching the impedance signature from the AC signal with the impedance signature of the oxygen concentration in the first fuel cell test stack; and
   calculating the hydrogen leak rate of the fuel cell stack by matching the oxygen concentration of the fuel cell stack with the impedance signature of the differential pressure of the second fuel cell test stack.

2. The method of claim 1 wherein the fuel cell stack has dimensions, the first fuel cell test stack has substantially similar dimensions to the dimensions of the fuel cell stack and the second fuel cell test stack has substantially similar dimensions to the dimensions of the fuel cell stack.

3. The method of claim 1 wherein the determining includes quantifying a rate of the hydrogen leak using a neural network.

4. The method of claim 1 wherein generating the first set of data points for impedance signatures of oxygen concentrations in the first fuel cell test stack includes:
   running the first test fuel cell stack at differing oxygen concentrations; and
   establishing the impedance signatures for the first set of data points based on the differing oxygen concentrations.

5. The method of claim 1 wherein generating the second set of data points for impedance signatures of differential pressures of hydrogen and oxygen in the second fuel cell test stack includes:
   running the second test fuel cell stack at differing oxygen concentrations; and establishing the impedance signatures for the second set of data points based on the differing oxygen concentrations.

6. A method, comprising:
    detecting a hydrogen leak in a polymer electrolyte membrane fuel cell stack;
    quantifying a rate of the hydrogen leak, the quantifying including:
        providing to a neural network a first set of data points that represent impedance signature values based on oxygen concentrations in a first fuel cell test stack, the first test stack having a first leak rate;
        providing a second set of data points that represent impedance signature values based on differential pressures of hydrogen and oxygen in a second fuel cell test stack, the second test stack having a second leak rate higher than the first leak rate of the first fuel cell test stack;
        generating a map by matching differential pressures from the second fuel cell test stack to oxygen concentrations from the first fuel cell test stack by matching the impedance signature values from the first fuel cell test stack with impedance signature values from the second fuel cell test stack;
        calculating the hydrogen leak rate of the fuel cell stack by identifying a differential pressure, the identifying of the differential pressure including:
            detecting an impedance value in the fuel cell stack based on an oxygen concentration; and
            using the map to identify the differential pressure using the impedance value of the oxygen concentration in the fuel cell stack.

7. The method of claim 6 wherein the quantifying includes:
    passing an AC signal through the fuel cell stack;
    detecting the impedance value, the impedance value being generated by the AC signal in the fuel cell stack;
    transmitting the impedance value to the neural network; and
    identifying the oxygen concentration and differential pressure corresponding to the impedance value using the map of the neural network.

8. The method of claim 6 wherein the fuel cell stack has a plurality of plates, each plate having a rectangular shape.

9. The method of claim 8 wherein the first test stack has a plurality of plates, each plate having the rectangular shape of the plates of the fuel cell stack.

10. The method of claim 9 wherein the second test stack has a plurality of plates, each plate having the rectangular shape of the plates of the fuel cell stack.

11. The method of claim 6 wherein the first set of data points and the second set of data points are established by running the first and second fuel cell test stacks at differing oxygen concentrations.

12. A fuel cell diagnostic apparatus that diagnoses a hydrogen leak in a fuel cell stack, the hydrogen leak having a rate, the apparatus comprising:
    a frequency response analyzer configured to apply an AC signal to the fuel cell stack and configured to measure an output impedance signature;
    a first fuel cell test stack having impedance signature values associated with oxygen concentrations;
    a second fuel cell test stack having impedance signature values associated with differential pressures of hydrogen and oxygen; and
    a neural network configured to receive the impedance signature values from the first fuel cell stack and the impedance signature values from the second fuel cell stack, the neural network configured to map the impedance signature values from the first fuel cell stack and the impedance signature values from the second fuel cell stack to each other, the neural network configured to identify an oxygen concentration from the map based on the output impedance signature and configured to output a differential pressure based on the oxygen concentration, and the neural network configured to calculate the rate of the hydrogen leak from the oxygen concentration and the differential pressure from the map.

* * * * *